(12) United States Patent
Kretschmar et al.

(10) Patent No.: US 7,554,003 B2
(45) Date of Patent: Jun. 30, 2009

(54) INVERTEBRATE ANIMAL MODEL WITH NEURODEGENERATIVE PHENOTYPE FOR SCREENING AND TESTING SUBSTANCES

(75) Inventors: Doris Kretschmar, Portland, OR (US); Jakob-Andreas Tschaepe, Heidelberg (DE)

(73) Assignee: Evotec Neurosciences GmbH, Hamburg (DE)

( * ) Notice: Subject to any disclaimer, the term of this patent is extended or adjusted under 35 U.S.C. 154(b) by 0 days.

(21) Appl. No.: 11/544,947

(22) Filed: Oct. 10, 2006

(65) Prior Publication Data
US 2007/0107070 A1    May 10, 2007

Related U.S. Application Data

(63) Continuation of application No. 10/501,815, filed as application No. PCT/EP02/03992 on Apr. 10, 2002, now abandoned.

(51) Int. Cl.
*A01K 67/00* (2006.01)
*A01K 67/33* (2006.01)
(52) U.S. Cl. ............... 800/8; 800/9; 800/12; 800/13
(58) Field of Classification Search ............... 800/8, 800/9, 13
See application file for complete search history.

(56) References Cited

FOREIGN PATENT DOCUMENTS

| WO | WO 01/20003 A2 | 3/2001 |
|---|---|---|
| WO | WO 02/057455 A2 | 7/2002 |
| WO | WO 03/028446 A2 | 4/2003 |

OTHER PUBLICATIONS

O'Brochta DA, Gene vector and transposable element behavior in mosqitoes, 2003, J. Experimental Biology, vol. 206, pp. 3823-3834.*
Nitasaka E, Repressor of P elements in *Drosophila melanogaster*: cytotype determination by a defective P element carrying only open reading frames 0 through 2, 1987, PNAS, vol. 84, pp. 7605-7608.*
Spradling AC, Gene disruptions in P transosable elements: an integral component of the *Drosophila* genome project, 1995, 92, pp. 10824-10830.*
Atkinson PW, Genetic transformation systems in insects, 2001, Annu. Rev. Entomol., vol. 46, pp. 317-346.*
Tschaepe et al., The EMBO J., 20002, vol. 21, pp. 6367-6376.*
Deak et al., 1997, Genetics, vol. 147, pp. 1697-1722.*
Chan et al. Cell Death and Differentiation (2000) 7, 1075-1080.*
Holschneider DP, Shih JC. Genotype to phenotype: challenges and opportunities. Int J Dev Neurosci. Oct. 2000;18(6):615-8.*
Leonard . Role of the common cytokine receptor gamma chain in cytokine signaling and lymphoid development. Immunol Rev. Dec. 1995; 148:97-114.*
Kretzschmar D. Neurodegenerative mutants in *Drosophila*: a means to identify genes and mechanisms involved in human diseases? Invert Neurosci. Nov. 2005;5(3-4):97-109.*
Penny et al. All neuropathies great and small. J Clin Invest. Nov. 2005;115(11):2968-71.*
Milan et al. A mutation in PRKAG3 associated with excess glycogen content in pig skeletal muscle. Science. May 19, 2000;288(5469):1248-51.*
Griffiths et al. Current concepts of PLP and its role in the nervous system. Microsc Res Tech. Jun. 1, 1998;41(5):344-58.*
Deak P et al: "P-Element Insertion Alleles of Essential Genes on the Third Chromosome of *Drosophilia melanogaster*: Correlation of Physical and Cytogenic Maps in Chromosomal Region 86E-87F" Genetics, Genetics Society of America, Austin, TX, US, vol. 147, No. 4 Dec. 1997, pp. 1697-1722 XP009009475 Issn: 0016-6731.
Fortini M E et al: "Modeling human neurodegenerative diseases in *Drosophilia*: on a wing and a prayer" Trends in Genetics, Elsevier, Amsterdam; NL, vol. 16, No. 4, Apr. 2000, pp. 161-167, XP004194020 ISSN: 0168-9525 p. 165, paragraph 3.
Tschäpe J-A et al: "The *Drosophilia* Mutant Löchrig (loe)—Neurodegeneration and Cholesterol Metabolism" Abstract Papers Presented at the 2001 Meeting on Neurobiology of *Drosophilia*, Oct. 2001, p. 201 XP001170306.
Tschäpe Jakob-Andreas et al: "The neurodegeneration mutant *löchrig* interferes with cholesterol homeostasis and *Appl* processing." EMBO (European Molecular Biology Organization) Journal, vol. 21, No. 23, Dec. 2, 2002, pp. 6367-6376, XP002239203 ISSN: 0261-4189.

* cited by examiner

*Primary Examiner*—Valarie Bertoglio
*Assistant Examiner*—David Montanari
(74) *Attorney, Agent, or Firm*—Jacobson Holman PLLC

(57) ABSTRACT

The present invention claims an invertebrate animal that has been modified to express a set of genes, the set comprising the gene coding for a modified version of the gamma subunit of AMP-activated protein kinase (AMPKg). According to the invention, the animal displays an identifiable phenotype related to lipid metabolism and neurodegeneration. This animal provides a model of neurodegenerative diseases, particularly Alzheimer's disease, and may be useful for screening and testing modulating agents, substances and therapeutic compounds for neurodegenerative disorders.

1 Claim, 7 Drawing Sheets

Figure 1:
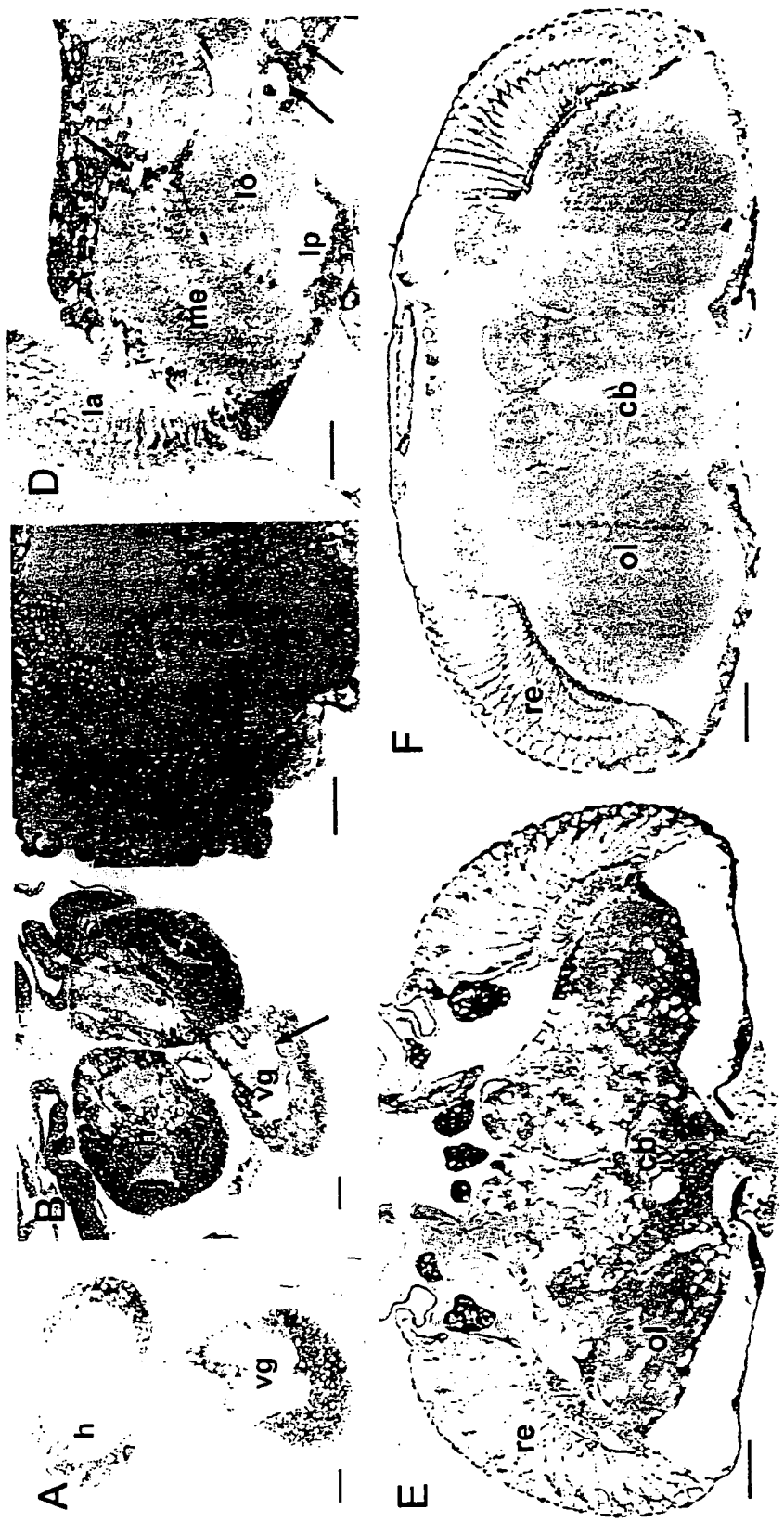

SEQUENCE LISTING

```
<160> NUMBER OF SEQ ID NOS: 2

<210> SEQ ID NO 1
<211> LENGTH: 76
<212> TYPE: PRT
<213> ORGANISM: Artificial Sequence
<220> FEATURE:
<223> OTHER INFORMATION: Description of Artificial Sequence: LOE I gene
      fragment (nucleotides 13 - 88) of Drosophila
      melanogaster

<400> SEQUENCE: 1

Lys Gln Gln Pro Leu Ala Asn Ala Pro Val Met Gly Val Gln Glu Asp
 1               5                  10                  15

Lys Ala Gln Glu Pro Lys Glu Leu Pro Asp Glu Pro Ala Lys Gln Pro
            20                  25                  30

Asp Gly Gln Pro Tyr Gln Ala Phe Ala Gly Glu Asp Ser Phe Glu Cys
        35                  40                  45

Ala Phe Glu Ser Thr Met Asp Asp Leu Glu Gln Gly Val Leu Asp Gly
    50                  55                  60

Tyr Glu Ser Asp Ser Glu Ala Ser Ala Asn Asp Gln
65                  70                  75

<210> SEQ ID NO 2
<211> LENGTH: 80
<212> TYPE: PRT
<213> ORGANISM: Artificial Sequence
<220> FEATURE:
```

-continued

```
<223> OTHER INFORMATION: Description of Artificial Sequence: X11 alpha
      gene fragment (nucleotides 37-116) from rat

<400> SEQUENCE: 2

Glu Gln Gln Pro Ser Pro Pro Pro Ala Gly His Ala Pro Glu Asp
 1               5                  10                  15

His Arg Ala His Pro Ala Pro Pro Pro Pro Pro Pro Glu Glu Glu
                20                  25                  30

Glu Glu Glu Arg Gly Glu Cys Leu Ala Arg Ala Ser Ser Thr Glu Ser
            35                  40                  45

Gly Phe His Asn His Thr Asp Thr Ala Glu Gly Asp Val Leu Ala Ala
    50                  55                  60

Ala Arg Asp Gly Tyr Glu Ala Glu Arg Ala Gln Asp Ala Asp Asp Glu
65                  70                  75                  80
```

INVERTEBRATE ANIMAL MODEL WITH NEURODEGENERATIVE PHENOTYPE FOR SCREENING AND TESTING SUBSTANCES

This is a continuation of Ser. No. 10/501,815, filed, May 11, 2005, now abandoned which is a 371 of PCT/EP02/03992, filed Apr. 10, 2002.

The present invention relates to an invertebrate animal model of neurodegenerative diseases with Alzheimer's disease-like pathological features. Such animal model may be useful in screening for and testing of substances and pharmaceutical agents that modulate plaque-formation related to neurodegenerative diseases, particularly Alzheimer's disease.

Neurodegenerative diseases, in particular Alzheimer's disease, have a severely debilitating impact on a patient's life. Furthermore, these diseases constitute an enormous health, social, and economic burden. Alzheimer's disease is the most common age-related neurodegenerative condition affecting about 10% of the population over 65 years of age and up to 45% over age 85 (for a recent review see Vickers et al., *Progress in Neurobiology* 2000, 60:139-165; the contents of all publications, patents and patent applications referred to and cited in the present invention shall be incorporated by reference in their entirety). Presently, this amounts to an estimated 12 million cases in the US, Europe, and Japan. This situation will inevitably worsen with the demographic increase in the number of old people ("aging of the baby boomers") in developed countries. The neuropathological hallmarks that occur in the brain of individuals suffering from Alzheimer's disease are senile plaques, composed of amyloid-b protein, and profound cytoskeletal changes coinciding with the appearance of abnormal filamentous structures and the formation of neurofibrillary tangles. AD is a progressive disease that is associated with early deficits in memory formation and ultimately leads to the complete erosion of higher cognitive function. Currently, there is no cure for AD, nor is there an effective treatment to halt the progression of AD or even a method to diagnose AD ante-mortem with high probability. Several risk factors have been identified that predispose an individual to develop AD, among them most prominently the epsilon4 allele of apolipoprotein E (ApoE). Although there are rare examples of early-onset AD which have been attributed to genetic defects in the genes for APP, presenilin-1, and presenilin-2, the prevalent form of late-onset sporadic AD is of hitherto unknown etiologic origin. The late onset and complex pathogenesis of neurodegenerative disorders pose a formidable challenge to the development of therapeutic and diagnostic agents. Therefore, it is very important to develop suitable animal models of neurodegenerative disease which may be useful in the development of such therapeutic and diagnostic agents.

Although the cholesterol metabolism has long been investigated, its role in neurodegeneration is still unclear. A connection between cholesterol and neurodegeneration has been made by the discovery that the apolipoprotein E4 (apo E4) allele is the major known risk factor for Alzheimer's disease (Saunders et al., 1993; Corder et al., 1993). ApoE4 has been strongly linked to both, the sporadic as well as familial late-onset form of Alzheimer's disease which account for approximately 99% of Alzheimer's cases (Weisgraber and Mahley, 1996, Neve and Robakis, 1998). ApoE is expressed in neurons and astrocytes and the first implication of apoE in Alzheimer's disease came from immunohistochemical studies, which revealed a localization of apoE in amyloid plaques and neurofibrillary tangles, the hallmarks of Alzheimer's disease (Namba et al., 1991).

ApoE is a component of several plasma and cerebrospinal fluid complexes which contain and transport lipids and cholesterol through the extracellular space by binding to the LDL or VLDL (low and very low density lipoprotein) receptors, a transport mechanism highly conserved in vertebrates and invertebrates (Fischer et al., 1999). ApoE-cholesterol-lipoprotein complexes are assembled from free cholesterol and are internalized by neurons via the LDL receptor pathway. After uptake they are degraded and the cholesterol released within the cell were it can either be used as free cholesterol or stored in the form of cholesterol ester (Poirier, 1994; Weisgraber and Mahley, 1996). The role of apoE4 in Alzheimer's disease is not yet clear but the well established function of apoE in lipid and cholesterol transport may be the crucial point. Studies have shown an inefficient cholesterol and phospholipid transport in Alzheimer brains resulting in an abnormal membrane lipid composition (Koudinova et al, 1996). In addition, the pathogenic Aβ peptide, which is produced from the amyloid precursor protein (APP) by cleavage through β-secretase, decreases cholesterol esterification and changes the distribution of free cholesterol in neurons (Koudinova et al., 1996; Liu et al., 1998). On the other side, the cleavage of APP by secretases is depending on the level of cholesterol (DeStrooper and Annaert, 2000). The cholesterol synthesis in neurons is regulated by hydroxy-methylglutaryl-CoA reductase (HMG-CoA). An inhibition of this enzyme not only reduces the cellular cholesterol level but also inhibits β-secretase cleavage of APP (Frears, et al, 1999). HMG-CoA activity is negatively regulated via phosphorylation through the AMP-activated protein kinase (AMPK), a heterotrimeric complex, consisting of the catalytic a subunit and a b and g subunit, found in all eukaryotes (Hardie et al., 1998, Kemp et al., 1999; GenBank accession numbers of the nucleotide sequence of *Drosophila* AMPKg: NM080509, AF094764; GenBank accession number of the protein sequence for *Drosophila* AMPKg: NP536757, AAC95306). In addition AMPK inhibits the activation of hormone-sensitive lipase, an enzyme involved in the breakdown of triglycerides and cholesterol ester (Garton et al., 1989).

It is an object of the present invention to provide an animal model useful for the screening and testing of modulating agents of neurodegenerative diseases, particularly Alzheimer's disease. Non-human mammalian animal models, such as primates and mice, etc., are expensive, may be difficult to use, suffer from a slow reproduction time with the generation of only small numbers of offspring, and require a lengthy period of time until late onset neurodegenerative symptoms and phenotypes can be observed. Therefore, there is a need for novel animal models having comparatively rapid reproduction cycles with large numbers of offspring. Such an animal would offer the advantage of simple and economic handling and would be ideally suited for screening and testing of modulating agents of neurodegenerative diseases. Of particular interest for this purpose are invertebrate animal models, in particular an invertebrate transgenic animal model of the fruit fly *Drosophila melanogaster* (see Fortini et al., 2000). Based on the surprising finding that the *Drosophila* mutant loechrig (loe), which is caused by a transposon insertion in the gene for the AMPK g subunit, is characterized by a low level of cholesterol ester together with strong neurodegenerative features, the present invention further provides methods and applications useful for the identification and testing of modulators, compounds and therapeutic agents for neurodegenerative diseases, particularly Alzheimer's disease. Furthermore, based on the genetic interaction of loe with beta amyloid protein precursor-like (Appl) which results in an aberrant processing of APPL, the present invention features a model system and methods of screening for substances that modulate the proteolytic processing of APP.

The singular forms "a", "an", and "the" as used herein and in the claims include plural reference unless the context dictates otherwise. For example, "a cell" means as well a plurality of cells, and so forth. The term "and/or" as used in the present specification and in the claims implies that the phrases before and after this term are to be considered either as alternatives or in combination. For instance, the wording "determination of a level and/or an activity" means that either only a level, or only an activity, or both a level and an activity are determined. The term "level" as used herein is meant to comprise a gage of, or a measure of the amount of, or a concentration of a transcription product, for instance an mRNA, or a translation product, for instance a protein or polypeptide. The term "activity" as used herein shall be understood as a measure for the ability of a transcription product or a translation product to produce a biological effect or a measure for a level of biologically active molecules. The term "activity" also refers to enzymatic activity. The terms "level" and/or "activity" as used herein further refer to gene expression levels or gene activity. Gene expression can be defined as the utilization of the information contained in a gene by transcription and translation leading to the production of a gene product. A gene product comprises either RNA or protein and is the result of expression of a gene. The amount of a gene product can be used to measure how active a gene is. The term "gene" as used in the present specification and in the claims comprises both coding regions (exons) as well as non-coding regions (e.g. non-coding regulatory elements such as promoters or enhancers, introns, leader and trailer sequences). The term "fragment" as used herein is meant to comprise e.g. an alternatively spliced, or truncated, or otherwise cleaved transcription product or translation product. A "modified version" of a gene can be understood as a fragment of a gene, or an alternative splice variant, or a gene comprising a modified nucleic acid sequence, said modified nucleic acid sequence comprising deletions, insertions, inversions, or mutations. The term "derivative" as used herein refers to a mutant, or an RNA-edited, or a chemically modified, or otherwise altered transcription product, or to a mutant, or chemically modified, or otherwise altered translation product. For instance, a "derivative" may be generated by processes such as altered phosphorylation, or glycosylation, or lipidation, or by altered signal peptide cleavage or other types of maturation cleavage. These processes may occur post-translationally. The term "modulator" as used in the present invention and in the claims refers to a molecule capable of changing or altering the level and/or the activity of a gene, or a transcription product of a gene, or a translation product of a gene. Preferably, a "modulator" is capable of changing or altering the biological activity of a transcription product or a translation product of a gene. Said modulation, for instance, may be an increase or a decrease in enzyme activity, a change in binding characteristics, or any other change or alteration in the biological, functional, or immunological properties of said translation product of a gene. The term 'AD' shall mean Alzheimer's disease.

Neurodegenerative diseases or disorders according to the present invention comprise Alzheimer's disease, Parkinson's disease, Huntington's disease, amyotrophic lateral sclerosis, Pick's disease, fronto-temporal dementia, progressive nuclear palsy, corticobasal degeneration, cerebro-vascular dementia, multiple system atrophy, and mild-cognitive impairment. Further conditions involving neurodegenerative processes are, for instance, ischemic stroke, age-related macular degeneration, and narcolepsy.

In one aspect, the present invention features a non-human animal that expresses a modified version of the gene coding for the gamma subunit of AMP-activated protein kinase (AMPKg). In a preferred embodiment, said animal is an invertebrate. Preferably, said animal is an insect, in particular a fly. The animal is preferably obtainable by a method selected from the group consisting of transposon insertion mutagenesis and chemical mutagenesis of the gene coding for the gamma subunit of AMP-activated protein kinase (AMPKg). It is preferred that said modified version of the gene coding for the gamma subunit of AMP-activated protein kinase (AMPKg) is the loechrig (loe) mutation.

In a further preferred embodiment, the expression of said gene results in an identifiable phenotype in said animal. The identifiable phenotype is related to lipid metabolism and/or is a neurodegenerative phenotype.

It is another preferred embodiment that the animal according to the present invention expresses a gene coding for an amyloid precursor protein, or a modified version thereof, in particular a fragment or a mutant thereof. It is desirable that said modified version of the gene coding for an amyloid precursor protein is a modified version of the gene coding for beta amyloid protein precursor-like (Appl) protein. It is further desirable that said modified version comprises a deletion, or a partial deletion, of the gene coding for beta amyloid protein precursor-like (Appl) protein, wherein said deletion, or partial deletion, results in a loss-of-function of said gene. In one embodiment of the present invention, it may be desirable that said animal is transgenic for a modified version of the gene coding for the gamma subunit of AMP-activated protein kinase (AMPKg) and/or a gene coding for an amyloid precursor protein, or a modified version thereof, in particular a fragment or a mutant thereof.

The animal, according to the present invention, is useful for identifying a modulator which affects lipid metabolism. It is further useful for identifying a modulator which affects a neurodegenerative phenotype. Another use of an animal according to the present invention is for identifying a modulator which affects processing of an amyloid precursor protein.

The present invention provides a method of identifying a modulator of lipid metabolism, and/or neurodegenerative phenotype, and/or amyloid precursor protein processing, comprising administering a substance, or a plurality of substances, to said animal; and observing the effect of said substance, or plurality of substances, on said animal. In a preferred embodiment, said substance, or plurality of substances, is orally administered to said animal.

In another aspect, there is provision for the use of an animal according to the present invention for identifying whether a gene, or a mutant thereof, is capable of modulating a phenotype related to lipid metabolism and/or neurodegeneration, in particular processing of an amyloid precursor protein. The modulation can be a suppression or an enhancement of said phenotype and/or processing of an amyloid precursor protein.

Other features and advantages of the invention will be apparent from the following description of figures and examples.

FIG. 1. Phenotype of the loe mutant. (A-E) Horizontal plastic brain sections stained with toloudine blue. (A) Brain sections from 1.instar larvae do not reveal any signs of degeneration. (B). In 3.instar larva vacuoles are forming in the active areas of the ventral ganglion (vg) and the central part of the brain (cb), while the newly forming optic system (ol) is free. (C) Sections through the brain of a stage P8 pupa appear wild type in contrast to brain sections from a pupa shortly before eclosion (D) where first vacuoles are visible (arrows).

(E) A 10 d old loe fly shows massive degeneration compared to (F) wild type. re, retina. Bar in A 15 µm, in B-D 50 µm.

Figure 2:
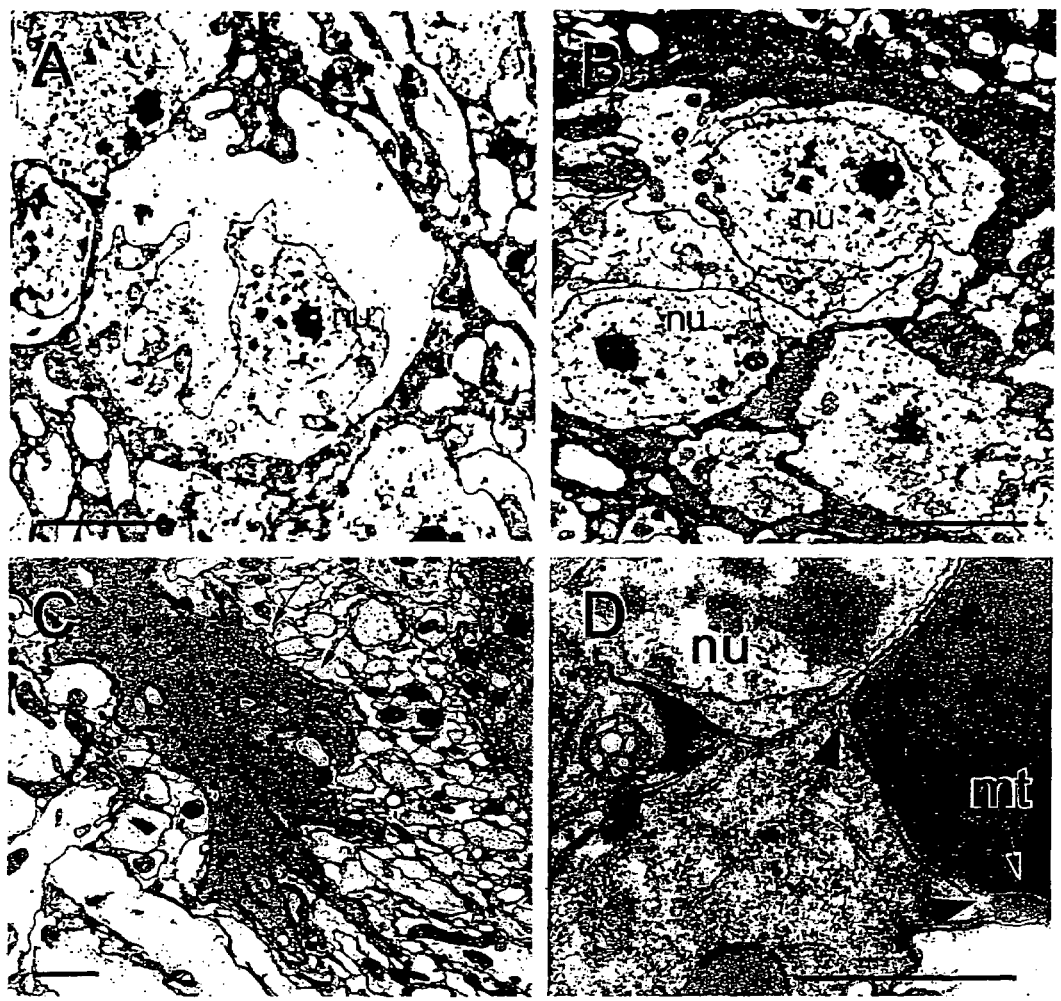

FIG. 2. Accumulation of fatty acids and necrotic cell death in loe. (A) EM brain sections from 7 d old loe flies reveal fatty inclusions (arrows). (B) The fatty acids seem to originate from within the cell because they are surrounded by residual cell cytoplasm (arrowheads), including a mitochondrium (mt). (C) Dying neurons, in this case monopolar cells of the optic system, in 7 d old loe flies show the characteristic swelling and lysis of necrotic cell death, while the nucleus (nu) stays intact. (D)Wild type monopolar cells. Bar 2 µm.

Figure 3:
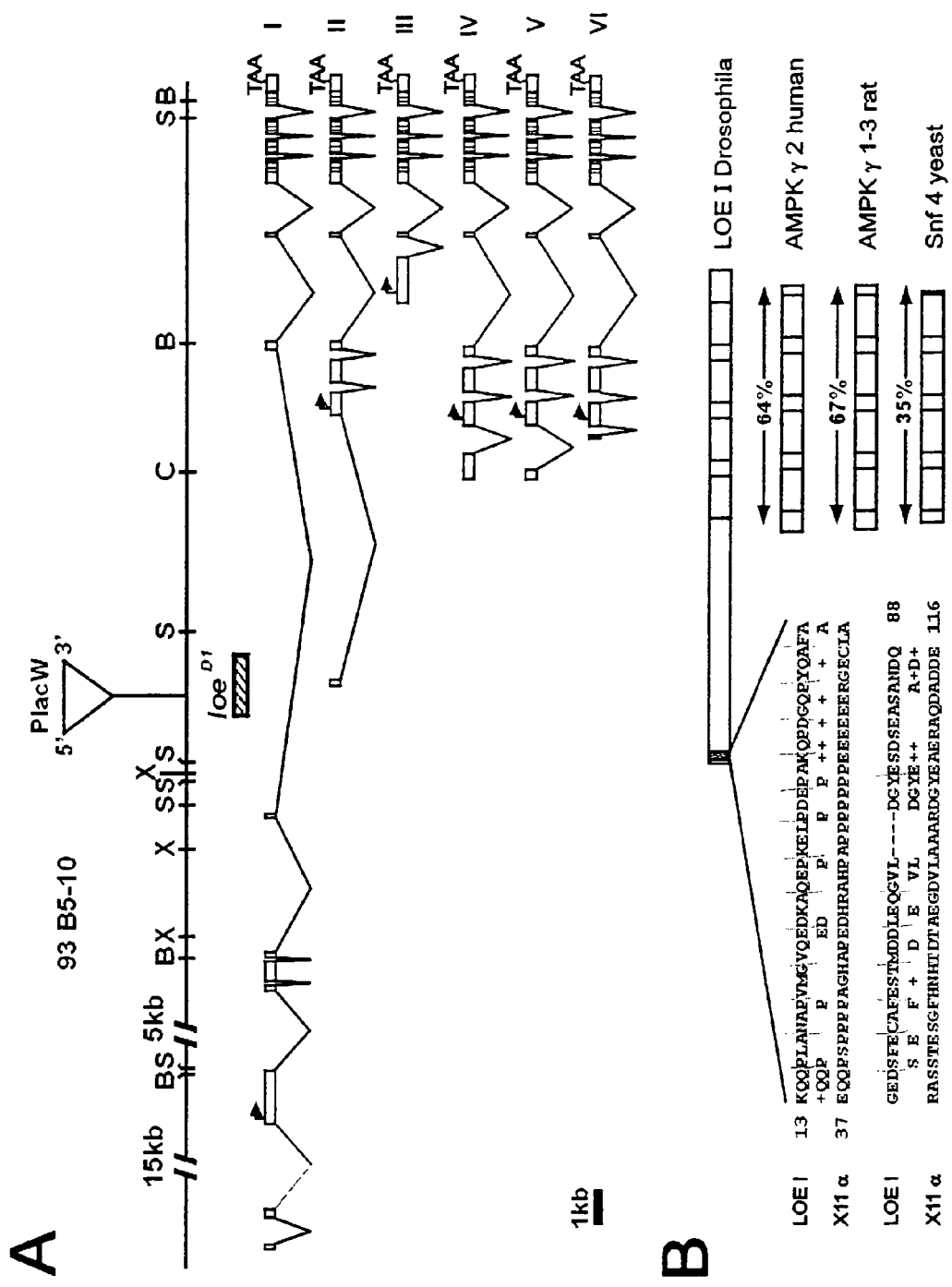

FIG. 3. Structural analysis of the loe gene. (A) Genomic region adjacent to the P-element (PlacW). The exon-intron structures of the various loe transcripts are shown underneath. Start codons are indicated by arrows. The deletion loe$^{D1}$ is indicated by a striped bar. B=BamH1, S=SstI, X=XbaI, C=ClaI. (B) The homology to other AMPK g-subunits is restricted to the C-terminus (only loeI shown), including the cystathionine-b-synthase domains (light gray). The identity is given above. The N-terminal fragment of LoeI (dark gray) shows homology to the rat X11a protein.

Figure 4:
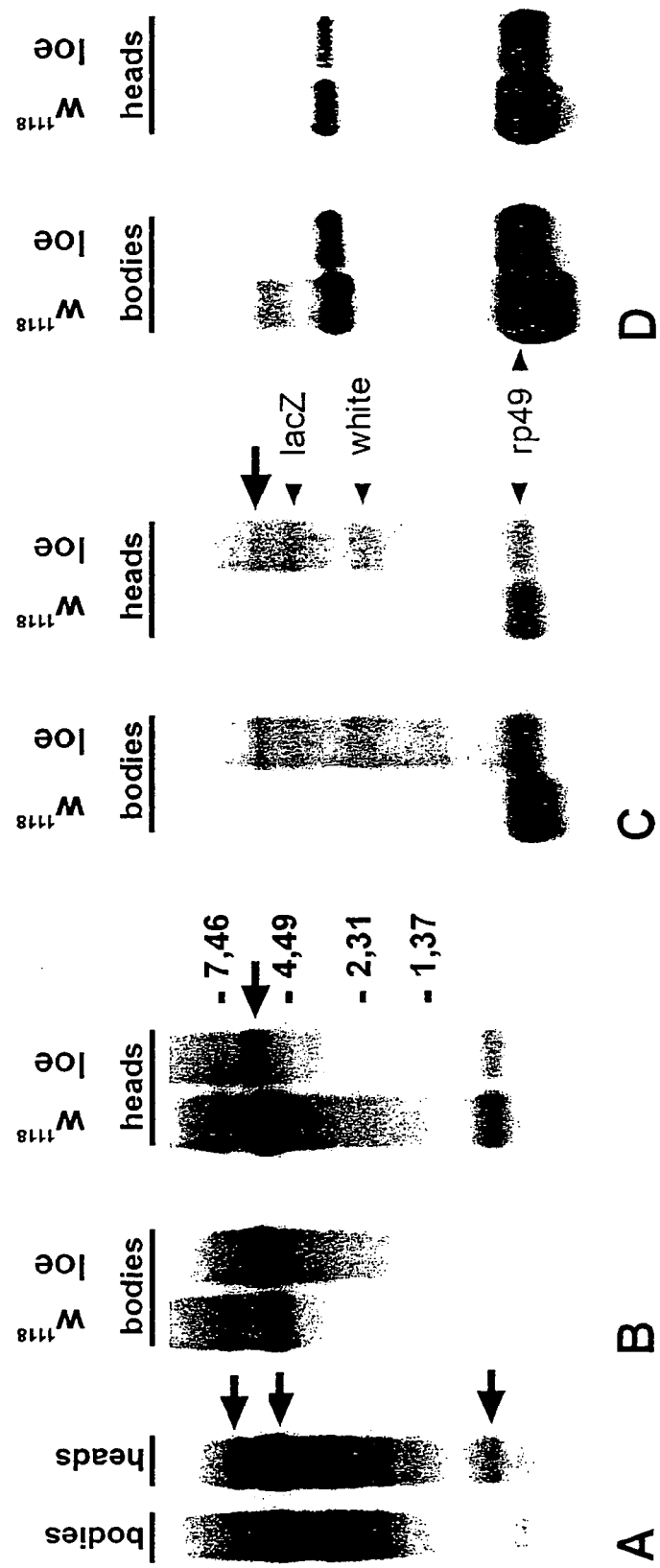

FIG. 4. Expression of loe mRNA. (A) Some transcripts, including three also detected with a probe derived from exon 1-3 of loeI (arrows and B) are specific or more abundant in heads compared to bodies of w$^{1118}$ flies. (B) Analysis of these transcripts reveals a larger fusion-transcript for the strongly expressed 4.7 kb form (arrow) in the loe mutant, which is also recognized by a P-element specific probe (C) (lacZ and white are transcripts encoded by the P-element, arrowheads). (D) The expression of loeII is unaltered. w$^{1118}$ was used as control because this line provides the same genetic background as the mutant. rp49 was used as loading control.

Figure 5:
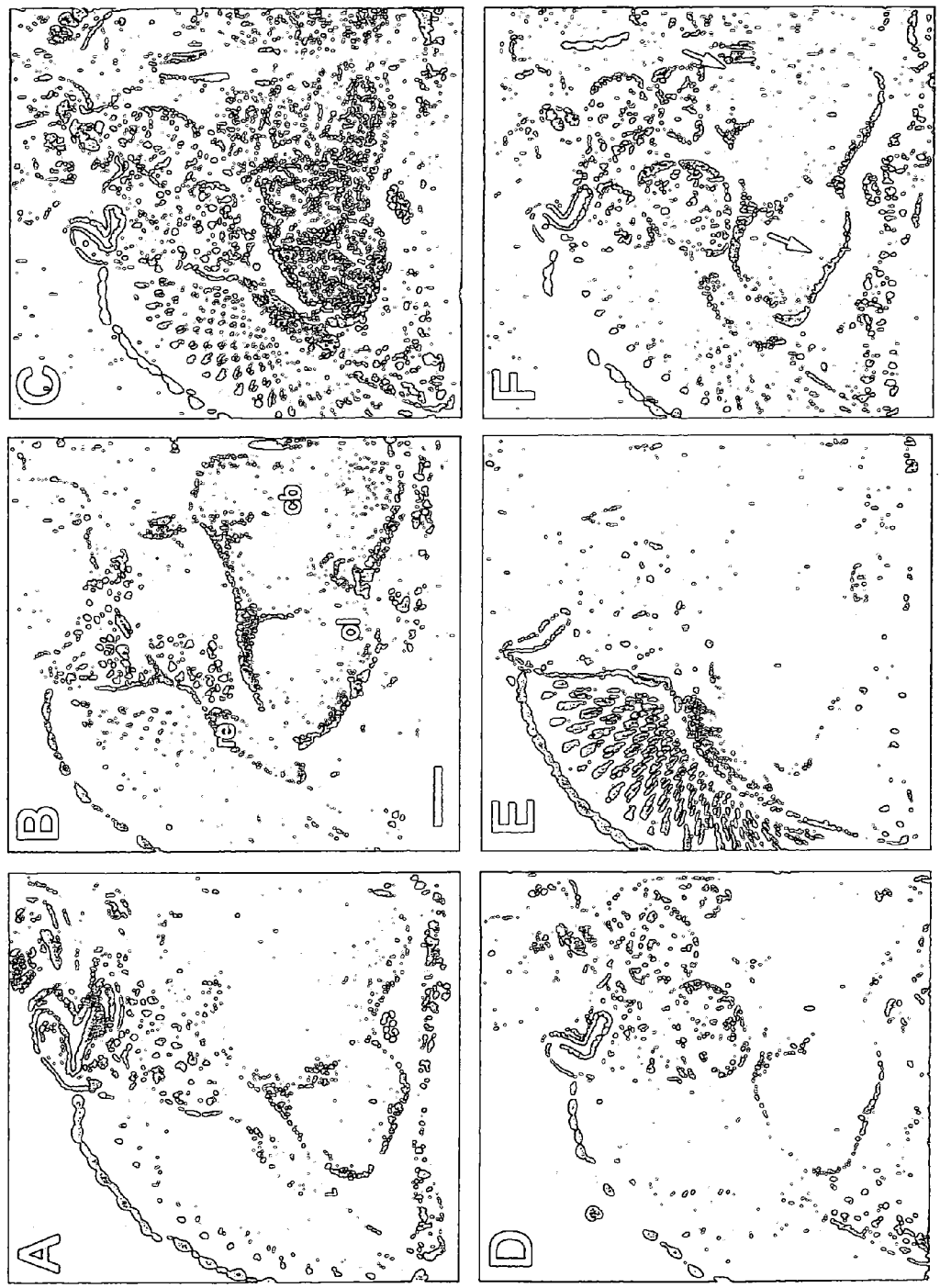

FIG. 5. loeI expression rescues the phenotype. Paraffin sections from 14 d old flies reveal the characteristic loe phenotype in (A) a control loe fly carrying only the UAS-loeI construct without the Gal4-driver construct. (B) Wild type. (C) Expressing loeII in neurons with elav-Gal4 does not rescue the phenotype. (D) In contrast, expression of loeI in neurons completely restores the wild type phenotype in loe. (E) A construct deleting the first 738aa of loeI, while leaving the conserved C-terminus intact, shows only partial rescue ability. (F) The construct without the X11a similar domain (deleting aa 1-319) reveals a better but still incomplete rescue, because some vacuoles are forming (arrows). re, retina; cb, central brain; ol, optic lobes. Bar 50 µm.

Figure 6:
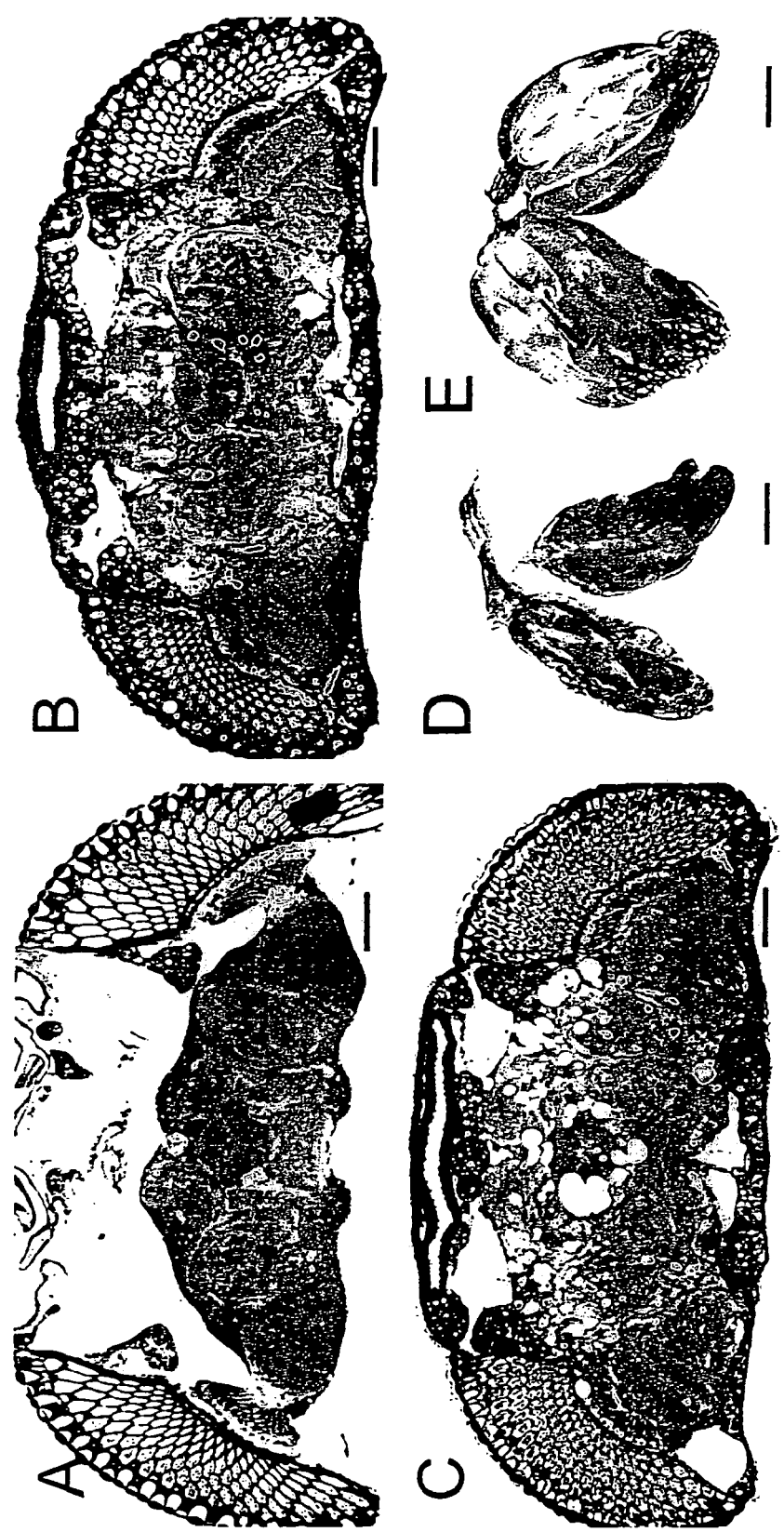

FIG. 6. Genetic interaction between loe and Appl. (A) A 4 d old Appl$^d$ mutant reveals no vacuolization, whereas loe at the same age displays many vacuoles (B). (C) In a 4 d old Appl$^d$; loe double mutant this phenotype is enhanced and more and larger vacuoles are formed. In addition female Appl$^d$; loe flies are sterile and have small ovaries (D) compared to wild type (E). Bar in A-C 50 µm, in D-E 150 µm.

Figure 7:
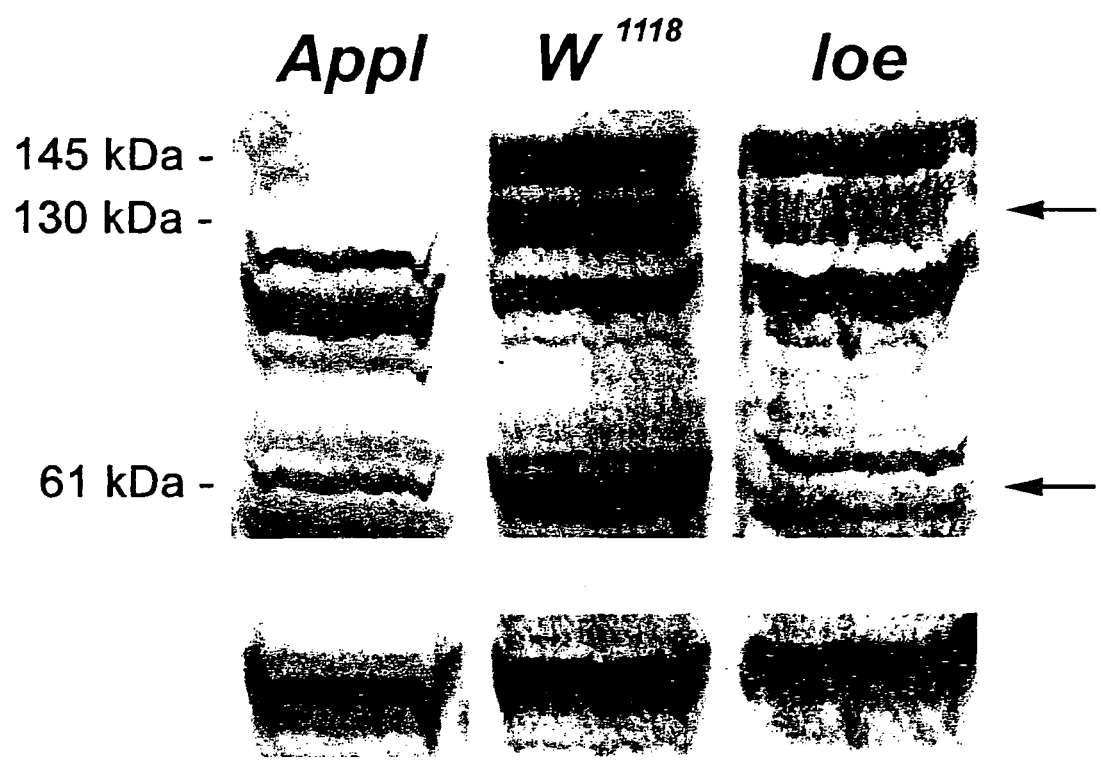

FIG. 7. Aberrant processing of APPL in loe. The APPL antiserum reveals in Western-blots, besides some unspecific bands, three specific APPL bands which are missing in the Appl mutant. Whereas the amount of the APPL precursor protein of 145 kDa is similar in loe flies compared to the control line w$^{1118}$, the amount of the secreted form of 135 kDa is decreased (upper arrow). The small form of 61 kDa is completely missing in loe mutants. The loading control, using an anti rasGAP antibody, is shown underneath.

EXAMPLE 1

Degeneration in Loe is Restricted to Differentiated Neurons:

The line löchrig (loe) was identified and isolated from a collection of P-element insertion lines from Deak et al. (1997). Approximately 800 lines which revealed a shortened adult life span were aged and screened histologically for signs of neurodegeneration. Two of these lines, with insertions at the same position, showed massive vacuolization of the central nervous system a few days after eclosion, which increased with aging. Vacuoles are most prominent around the central complex and in the central parts of the brain whereas the optic lobes are less affected (FIG. 1E). Electron microscopic analysis revealed the accumulation of a fatty substance (FIG. 2A), presumably unsaturated fatty acids due to the stabilization by osmium (Ruthmann, 1966), which originates in the cell cytoplasm (FIG. 2B). To determine whether the degeneration is restricted to the adult CNS we examined various developmental stages for signs of degeneration and abnormal cell death. We could not detect any vacuoles or other degenerative defects in the brains from 1. instar larvae, suggesting that the embryonic development is undisturbed (FIG. 1A). In 3. instar larvae however vacuolization is clearly visible in the hemispheres as well as the ventral ganglia of the CNS. Interestingly, the degeneration is restricted to the central half of the hemispheres (FIG. 1B), an area which shows neuronal activity in larvae. In contrast, the newly developing optic system is free of vacuoles. Examination during pupal development revealed that pupal brains from stage P8 (Bainbridge and Bownes, 1981) were free of vacuoles (FIG. 1C) whereas pupae shortly before eclosion (P15) showed first vacuoles in the central brain (FIG. 1D, arrows). These results indicate that the vacuolization and degeneration in loe is confined to differentiated, probably synaptic active neurons, whereas neuroblast and developing neurons are unaffected.

To assess whether dying cells undergo apoptotic or necrotic cell death we performed TUNEL stainings (Gavrieli et al., 1992) and electron microscopic studies. The observed swelling and lysis of cell bodies, while the nucleus stays intact, are characteristic features for a necrotic cell death (FIG. 2C), which is also supported by the negative TUNEL staining on head cryosections. In addition, the EM sections confirmed that the dying cells are neurons because glial cells appeared morphologically wild type.

Loe Encodes a Subunit of the AMP Dependent Protein Kinase Complex:

To verify that the mutation is caused by the insertion of the P-element we remobilized the P-element (O'Kane, 1998) to restore the wild type phenotype. From 100 established lines 95 showed a reversion of the vacuolization phenotype in paraffin head sections. 30 of these lines were characterized in more detail, revealing a precise excision of the P-element in two of the revertant lines. These results confirm the mutagenic effect of the P-element, which was consequently used to isolate neighboring genes via plasmid rescue (O'Kane, 1998).

We could isolate approximately 20 kb genomic DNA adjacent on either side of the P-element insertion site performing plasmid rescues. Within this region we found homology to a first cDNA fragment from the Berkeley Sequencing Project and to genomic clones from the Drosophila Genome Project. Various other cDNAs were isolated by their homology to either of these clones. Their further characterization revealed that they represent at least six alternatively spliced transcripts for the Drosophila gamma subunit of AMP activated protein kinase (AMPK) (FIG. 3A). The different mRNAs encode at least three different protein isoforms, all sharing the same C-terminus while varying in their N-terminal part. The C-terminus includes the so-called CBS (cystathionine-b-synthase) domains which are highly conserved between the Drosophila, yeast and mammalian proteins (FIG. 3B). Interestingly, a region in the unique N-terminus of the LoeI isoform shows homology to the X11a protein which can bind to the Ab peptide of APP (Borg et al., 1998); loeI and X11a are 28% identical and 41% similar over a stretch of 80 amino acids (FIG. 3B). The P-element is inserted in the seventh intron of this transcript and 38 bp upstream of the transcription start site of loeII (FIG. 3A), suggesting that one or both transcripts are affected by the insertion (all other transcripts are localized more than 10 kb downstream of the insertion site and are therefore most likely not affected by the P-element). We created a small deletion of 1.3 kb around the insertion site, removing exon 1 of the loeII transcript (FIG. 3A, loe$^{D1}$) and these flies do not show a degeneration phenotype. This indicates that loeII is not required for CNS integrity.

The Mutation is Due to an Aberrant LoeI Transcript:

Northern blot analysis of adult body and head mRNA fractions further supported that the mutation is due to an effect on the loeI transcript. Using a probe complementary to the conserved 3' ends of loe reveals several transcripts, some of them enriched in heads compared to bodies (FIG. 4A). A probe comprising exon 1-3 from loeI detected three of these transcripts (FIG. 4A, arrows, 4B), with a size of 7.6 kb, 4.7 kb (the size of the cDNA), and 0.7 kb. Comparing transcripts in head homogenates from wild type and loe mutant flies revealed a change of only the 4.7 kb loeI transcript, increasing it in size to approximately 5.5 kb in the mutant (FIG. 4B, arrow). The hybridization of this aberrant transcript with a P-element specific probe proves that it is due to splicing parts of the P-element into the loeI transcript (FIG. 4C). Other transcripts, including loeII, are not altered in mutant flies (FIG. 4D).

To finally confirm the role of loeI, we expressed the loeI and loeII cDNA in different cell types using the UAS/Gal4 system (Brand and Perrimon, 1993). Lines carrying P-element vectors with either the loeI or loeII cDNA under the control of the Gal4 binding sequence (UAS) were crossed with various Gal4 lines to induce expression of loe in different cell types. A rescue of the loe phenotype could only be achieved by using the neuron specific elav-Gal4 line (Luo et al., 1994) in combination with UAS-loeI (FIG. 5D). Expression in glia with the loco-Gal4 line (Granderath et al., 2000) did not rescue the phenotype nor did expression of loeII in neurons (FIG. 5C). This finally proves that the mutation is caused by a disruption of only the loeI transcript. In addition, these experiments reveal a requirement for this transcript in neurons because glial expression can not rescue the phenotype.

The Unique N-Terminus of LoeI is Required for Wild Type Function:

To further investigate the function of the transcript specific N-terminal region we created shortened loeI constructs. Expression in neurons of a construct deleting aa 1-738, leaving the conserved C-terminus intact, could only partially improve the phenotype (FIG. 5E). This confirms the importance of the unique N-terminus for the specific function of the LoeI protein. A deletion of the X11a similar domain and the more N-terminal part (aa 1-319) could rescue the phenotype to a much better extend, however we could still detect some vacuoles (FIG. 5F). The X11a similar domain is therefore required for wild type function but other functional important domains must reside within the N-terminus of loeI because deleting more results in a much more incomplete rescue.

Loe is Involved in Cholesterol Homeostasis:

To assess whether the loe mutation influences the cholesterol metabolism, a role well described for AMPK (Kemp et al., 1999), we measured the lipid composition of fly heads. The analysis of phospholipids and free cholesterol did riot reveal any significant differences between wild type and mutant flies. The amount of cholesterol ester, however was reduced by approximately 40% (mean value from 9 measurements). Expressing loeI in neurons restored the wild type level of cholesterol ester. This strongly suggests a connection between cholesterol homeostasis and neurodegeneration in the loe mutant. AMPK inhibits the activation of hormone-sensitive lipase, an enzyme involved in the breakdown of cholesterol ester in many tissues other than the brain (Garton et al., 1989). A cholesterol ester hydrolase is also described for the brain (Gosh and Grogan, 1990), however, so far nothing is known whether this enzyme is regulated by AMPK. If a similar pathway exists in the brain the missing inhibition by AMPK might lead to an overactivity of this hydrolase and therefore to the reduced level of cholesterol ester in the loe mutant.

Loe Interacts with Amyloid Precursor Protein Like:

As mentioned above cholesterol ester has been involved in the processing of Ab from APP, and also X11a has been connected with Ab. We looked for interactions between loe and the β-amyloid protein precursor-like (Appl) gene, the fly homolog of the human APP (Rosen et al., 1989). Appl$^d$ mutants, which carry a deletion in the Appl gene, (Torroja et al.,1996) alone do not reveal any signs of neurodegeneration (FIG. 6A). However, crossing Appl$^d$ with loe flies shows an enhancement of the vacuolization (FIG. 6B, C). The effect is weaker in Appl$^d$ heterozygous double mutants than in Appl$^d$ homozygous ones. This reveals for the first time an involvement of an APP null allele with neurodegeneration. In addition females homozygous for both mutations are sterile and have small ovaries with only a few ovarioles (FIG. 6D), while neither loe nor Appl$^d$ are sterile or have small ovaries (data not shown). A function in ovaries has also been suggested for the human APP which is highly expressed in follicle cells where it may take part in membrane turnover and trafficking (Beer et al., 1995).

To determine whether this genetic interaction might be connected to an aberrant processing of APPL in the loe background we performed Western blot analysis of brain extracts. Using an anti-APPL polyclonal antibody (Torroja at al., 1996) we detect three bands in w$^{1118}$, representing the genetic background used to induce the loe mutation.(FIG. 7). The bands correspond to the membrane-associated precursor of 145 kDa, the 130 kDa secreted form (Luo et al., 1990) and a small form of approximately 61 kDa, which are all not detectable in Appl$^d$. In the loe mutant we find similar amounts of APPL precursor protein. However, the level of the processed secreted form is reduced and the small form is missing completely. This confirms a role of loe in APPL processing, presumably by the alteration in cholesterol ester and the consequent changing environment for the membrane bound secretases. In addition it suggests a neuroprotective function of APPL, or specifically its processed forms, which are severely decreased in loe. The complete loss of APPL in the double mutant further enhances the neurodegenerative phenotype.

The AMP-activated protein kinase (AMPK) is a central component of a protein kinase cascade conserved in eukaryotes (Kemp et al., 1999; Hardie et al., 1998). This enzyme acts as a metabolic sensor to monitor the cellular AMP and ATP levels and is activated by various stress situations such as starvation or hypoxia. AMPK modulates many aspects of cell metabolism (Winder and Hardie, 1999). Its major function described so far is to activate energy providing mechanisms while inactivating energy consuming processes in case of ATP depletion. Although the brain has a particularly high metabolic activity nothing was known so far about the requirement of AMPK in this tissue.

AMPK is a heterotrimer, consisting of the catalytic a subunit and a b and g subunit which are required for stabilization of the complex and kinase activity. The activity of the complex is regulated by phosphorylation through an upstream kinase and both phosphorylation as well as dephosphorylation are sensitive to AMP (Davies et al., 1995). For all three subunits different isoforms were identified which assemble to specific AMPK complexes with distinguishable tissue distribution in vertebrates (Stapleton et al., 1996; Thornton et al, 1998). Whether these different AMPK isoforms have distinguishable physiological functions is still unclear. In contrast to vertebrates where various isoforms are encoded by separate genes, the *Drosophila* g subunits are created by alternative splicing because we could not identify additional genes in the *Drosophila* Genome Project. Surprisingly, the *Drosophila* loe proteins contain domains not described in other species so far. That these domains play a pivotal role for the specific function of the different splice forms is shown by the rescue experiments using different splice forms and deletion constructs which do not or only partially restore the wild type function. In addition, the failing rescue experiments suggest that the function of the various isoforms goes beyond the regulation of the energy demand and very likely the same applies to vertebrate isoforms.

The vacuolization in loe is accompanied by the accumulation of fatty acids. One of the targets identified for AMPK is acetyl-CoA carboxylase which catalyzes a key step in fatty acid synthesis. It has been show that activation of AMPK inhibits fatty acid synthesis (Hardie et al., 1998). This suggests of course an increased fatty acid synthesis when AMPK is inactive, and the accumulation of fatty acids in loe is therefore in good agreement with the role of AMPK in fatty acid synthesis in cell culture.

AMPK has a central role in the cholesterol metabolism by regulating HMG-CoA reductase which is the key regulator for the biosynthesis of cholesterol, and hormone-sensitive lipase which is involved in the breakdown of cholesterol ester (Garton et al., 1989). Both are negatively regulated by AMPK which can therefore inhibit the synthesis of cellular cholesterol as well as control the storage and recycling in form of cholesterol ester. The reduced level of cholesterol ester in loe mutants confirms the influence of AMPK on cholesterol homeostasis shown in cell culture (Hardie et al., 1998, Kemp et al., 1999). The effect on cholesterol ester, while free cholesterol is unaffected, could be due to a specific influence of loe on the regulation of a cholesterol ester hydrolase like hormone-sensitive lipase. However, free cholesterol might be effected as well, but a decrease could rapidly be counterbalanced by recycling from cholesterol ester. Synthesis, transport and recycling of cholesterol is tightly connected, and therefore detailed studies have to be done to determine which pathway is influenced directly by loe.

The present invention discloses that the loe mutation effects APPL processing, decreasing the amount of secreted APPL. It has recently been shown that lowering the cholesterol concentration inhibits APP cleavage by b-secretase and interferes with the localization of APP in so-called rafts (Simons, et al. 1998, Frears, et al. 1999). These are membrane microdomains consisting of lipids, proteins and cholesterol and their correct composition seams to be required for APP processing (DeStrooper and Annaert, 2000, Drouet et al., 2000). We suggests a similar effect in our loe mutant in vivo, where an aberrant membrane composition, due to the lowered level of cholesterol ester, decreases the production of secreted APPL. The loe mutant not only influences APPL processing but also interacts genetically with the $Appl^d$ null allele. $Appl^d$ as well as knock-outs of APP in mice only display subtle neurological deficits (Luo et al., 1992, Müller et al., 1994, Zheng et al., 1995). In the background of the loe mutation we can describe for the first time a neurodegenerative phenotype for a null mutation in one of the members of the APP family. The enhancement of the vacuolization phenotype of loe by $Appl^d$ reveals that wild type APPL and perhaps especially its secreted form, which is already decreased in loe, has a neuroprotective function.

Materials and Methods

*Drosophila* stocks: All stocks were maintained and raised under standard conditions. Canton S wild type and $w^{1118}$ were used as control stocks.

Tissue sections for light and electron microscopy: Larval brains and pupal and adult heads were prepared for light and electron microscopy as described in Kretzschmar et al. (1997). For light microscopy, 1 µm serial sections were cut and stained with 1% toluidine blue, 1% Borax. Ultrathin Epon plastic sections were postfixed with osmium and stained with 2% uranyl acetate, followed by Reynolds' lead citrate (Reynolds, 1963), and stabilized for transmission electron microscopy by carbon coating. Examination was done with a Zeiss EM10C/VR electron microscope at 40-80 kV. Parrafin mass histology was performed as described by Jäger and Fischbach (Ashburner, 1989).

Cloning and sequencing: The cDNA clones for the various loe transcripts and genomic clones were isolated from the *Drosophila* Genome Project (cDNAs:# SD02114, LD45665, LD28468, SD02088, GH16589, LD19285, LD41424, GH28591, LD05242, LD13337 and GH08914). The pIndy5 (kindly provided by L. Seroude) and pCaSpeR3-UAS (pUAST, Flybase) vectors were used for the pUAS-loe constructs. Sequencing was performed using the Thermo Sequenase fluorescent labeled primer cycle sequencing kit from Amersham Pharmacia after subcloning cDNA fragments into pBluscript KS. Reactions were done on a Hybaid Omn-E (MWG) thermocycler according to the instruction manual for the sequencing kit. Sequence analysis followed with the ALFexpress sequencing system (Pharmacia) using Hydrolink Long Ranger gels (FMC Bio Products).

Northern blots: Total RNA was isolated using the Trizol method described in Goodwin et al., 1997 and poly mRNA selected with the Promega PolyAtract system. Northern blots were performed following the protocol of Ausubel et al., 1996.

Lipid and sterol measurements: 2 mg of fly heads were homogenized mechanically and chloroform/methanol extracted as described in Folch et al., 1957. Phospholipids were separated by two-dimensional thin-layer chromatography on Silica gel 60 plates (Merck) using chloroform/methanol/25% NH3 (65:35:5; per vol.) and chloroform/acetone/methanol/acetic acid/water (50:20:10:10:5; per vol.) as solvents. Phospholipids were visualized on TLC plates by staining with iodine vapor, then scraped off and quantified (Broekhyse, 1968). For the analysis of neutral lipids, extracts were applied to Silica gel 60 plates with a sample applicator (Linomat IV; CAMAG) and chromatograms developed in an ascending manner using the solvent system light petroleum/diethyl ether/acetic acid (70:30:2; per vol.). Quantitation of sterol and sterol ester was carried out by densitometric scanning at 275 nm with ergosterol as standard. Neutral lipids were visualized by post-chromatographic staining using a chromatogram immersion device (CAMAG). Quantitation of sterol and sterol esters was carried out by densitometric scanning at 275 nm with ergosterol as standard. Quantification of triacylglycerols, sterol and sterol ester was carried out by densitometric scanning at 400 nm with triolein.

Western blot analysis: Fly heads were homogenized as described in Torroja et al., 1996 and loaded on 7.5% SDS-PAGE gels using standard methods (Laemmli, 1970). Proteins were transferred onto nitrocellulose membranes (Towbin et al., 1979). Immunoreactions with anti-APPL (Ab952, kindly provided by K. White), diluted 1:300 and preadsorbed over night against Appl$^d$ embryos, was done following the manufacturer's protocol for ECL Western Blot Detection System (Amersham). Hybridoma supernatant was diluted 1:3 for detecting rasGAP as the loading control.

REFERENCES

Ausubel, F. M., Brent, R., Kingston, R. E., Moore, D. D., Seidman, J. G., Smith, J. A. and Struhl, K. (1996). Current Protocols in Molecular Biology, New York: John Wiley & Sons.

Bainbridge, S. P. and Bownes, M. (1981). Staging the metamorphosis of *Drosophila melanogaster.* J. Embryol. Exp. Morphol. 66, 57-80.

Beer, J., Masters, C. L. and Beyreuther, K. (1995). Cells from peripheral tissue that exhibit high APP expression are characterized by their high membrane fusion activity. Neurodegeneration 4, 51-59.

Borg, J. P., Yang, Y., De Taddeo-Borg, M., Margolis, B. and Turner, R. S. (1998). The X11alpha protein slows cellular amyloid precursor protein processing and reduced Ab40 and Ab42 secretion. J. Biol. Chem. 273, 14761-14766.

Brand, A. H. and Perrimon, N. (1993). Targeted gene expression as a means of altering cell fates and generating dominant phenotypes. Development 118, 401-415.

Broekhuyse, R. M. (1968). Phospholipids in tissues of the eye. Isolation, characterization and quantitative analysis by two-dimensional thin-layer chromatography of diacyl and vinyl-ether phospholipids. Biochim. Biophys. Acta 260, 449-459.

Corder, E. H., Saunders, A. M., Strittmatter, W. J., Schmechel, D. E., Gaskell, P. C., Small, G. W:, Roses, A. D., Haines, J. L. and Pericak-Vance, M. A. (1993). Gene dose of apolipoprotein E type 4 allele and the risk of Alzheimer's disease in late onset families. Science 261, 921-923.

Davies; S. P., Helps, N. R., Cohen, P. T. and Hardie, D. G. (1995). 5'-AMP inhibits dephosphorylation, as well as promoting phosphorylation, of the AMP-activated protein kinase. Studies using bacterially expressed human protein phosphatase-2C alpha and native bovine protein phosphatase-2AC. FEBS Lett. 377, 421-421.

Deak, P., Omar, M. M., Saunder, R. D., Pal, M., Komonyi, O., Szidonya, J., Maroy, P., Zhang, Y., Ashburner, M., Benos, P., et al. (1997). P-element insertion alleles of essential genes on the third chromosome of *Drosophila melanogaster:* correlation of physical and cytogenetic maps in chromosomal region 86E-87F. Genetics 147, 1697-1722.

DeStrooper, B. and Annaert, W. (2000). Proteolytic processing and biological functions of the amyloid precursor protein. J. Cell Sci. 113, 1857-1870.

Drouet, B., Pincon-Raymond, M., Chambaz, J. and Pillot, T. (2000). Molecular basis of Alzheimer's disease. Cell. Mol. Life. Sci. 57, 705-715.

Fisher, C. A, Kiss, R. S., Francis, G. A., Gao, P. and Ryan, R. O. (1999). Human apolipoprotein E N-terminal domain displacement of apolipophorin III from insect low density lipophorin creates a receptor-competent hybrid lipoprotein. Comp. Biochem. Physiol. Biochem. Mol. Biol. 122, 447-451.

Folch, J., Lees, M. and Sloane-Stanley, G. H. (1957). A simple method for the isolation and purification of total lipids from animal tissues. J. Biol. Chem. 226, 497-509.

Fortini M. E. and Bonini N. M. (2000). Modeling human neurodegenerative diseases in *Drosophila:* on a wing and a prayer. Trends Genet 16, 161-7.

Frears, E. R., Stephens, D. J., Walters, C. E., Davies, H. and Austen, B. M. (1999). The role of cholesterol in the biosynthesis of beta-amyloid. Neuroreport 10, 1699-1705.

Garton, A. J., Campell, D. G., Carling, D., Hardie, D. G., Colbran, R. J. and Yeaman, S. (1989). Phosphorylation of bovine hormone-sensitive lipase by the AMP-activated protein kinase. A possible antilipolytic mechanism. Eur. J. Biochem. 179, 249-254.

Gavrieli, Y., Sherman, Y. and Ben-Sasson, S. A. (1992). Identification of programmed cell death in situ via specific labeling of nuclear DNA fragmentation. J. Cell Biol. 119, 493-501.

Goodwin, S. F., Del Vecchio, M., Velinzon, K., Hogel, C., Russell, S. R., Tully, T. and Kaiser, K. (1997). Defective learning in mutants of the *Drosophila* gene for a regulatory subunit of cAMP-dependent protein kinase. J Neurosci. 17, 8817-8827.

Gosh, S. and Grogan, W. M. (1990). Activation of myelin-associated cholesteryl ester hydrolase in developing rat brain. Brain Res. Dev. Brain Res 54, 147-149.

Granderath, S., Bunse, I. and Klämbt, C. (2000). gcm and pointed synergistically control glial transcription of the *Drosophila* gene loco. Mech. Dev. 91, 197-208.

Hardie, D. G., Carling, D. and Carlson, M. (1998). The AMP-activated/SNF1 protein kinase subfamily: Metabolic sensor of the eukaryotic cell. Annu. Rev. Biochem. 67, 821-855.

Jäger, R. J. and Fishbach, K. F. in Ashburner, M. (1989). *Drosophila:* A laboratory manual. Cold Spring Harbor, N.Y.: Cold Spring Harbor Laboratory Press.

Kemp, B. E., Mitchell, K. I., Stapleton, D., Michell, B. J., Chen. Z.-P. and Witters, L. (1999). Dealing with energy demand: the AMPK-activated protein kinase. TIBS 24, 22-25.

Koudinova, N. V., Berezov, T. T. and Koudinov, A. R. (1996). Multiple inhibitory effects of Alzheimer's peptide Ab1-40 on lipid biosynthesis in cultured human HepG2 cells. FEBS Lett. 395, 204-206.

Kretzschmar D., Hasan G., Sharma S., Heisenberg M. and Benzer S. (1997). The swiss cheese mutant causes glial hyperwrapping and brain degeneration in *Drosophila.* J. Neurosci. 17, 7425-7432.

Laemmli, U. K. (1970). Cleavage of structural proteins during the assembly of the head of bacteriophage T4. Nature 227, 680-685.

Liu, Y., Peterson, D. A. and Schubert, D. (1998). Amyloid b peptide alters intracellular vesicle trafficking and cholesterol homeostasis. Proc. Natl. Acad. Sci. 95, 13266-13271.

Luo, L., Liao, Y. J., Jan, L. Y. and Jan, Y. N. (1994). Distinct morphogenetic functions of similar small GTPases: *Drosophila* Drac1 is involved in axonal outgrowth and myoblast fusion. Genes Dev. 8, 1787-1802.

Luo, L., Tully, T. and White, K. (1992). Human amyloid precursor protein ameliorates behavioral deficit of flies deleted for Appl gene. Neuron 9, 595-605.

Müller, U., Cristina, N., Li, Z. W., Wolfer, D. P., Lipp, H. P., Rulicke, T., Brandner, S., Aguzzi, A. and Weissmann, C.

(1994). Behavioral and anatomical deficits in mice homozygous for a modified b-amyloid precursor protein gene. Cell 79, 755-765.

Namba, Y., Tomonaga, M., Kawasaki, H., Otomo, E. and Ikeda, K. (1991). Apolipoprotein E immunoreactivity in cerebral amyloid deposits and neurofibrillary tangles in Alzheimer's disease and kuru plaque amyloid in Creutzfeldt-Jakob disease. Brain Res. 541, 163-166.

Neve, R. L. and Robakis, N. K. (1998). Alzheimer's disease: a re-examination of the amyloid hypothesis. TINS 21, 15-19.

O'Kane, C. J. in: Roberts, D. B. (1998). *Drosophila:* A practical approach. 2.ed. Oxford University Press, New York.

Perez, R. G., Zheng, H., Van der Ploeg, L. H. and Koo, E. H. (1997). The b-amyloid precursor protein of Alzheimer's disease enhances neuron viability and modulates neuronal polarity. J Neurosci 17, 9407-9414.

Poirier, J. (1994). Apolipoprotein E in animal models of CNS injury and in Alzheimer's disease. TINS 17, 525-530.

Reynolds, E. S. (1963). The use of lead citrate at high pH as an electron-opaque stain in electron microskopy. J. Cell Biol. 17, 208-212.

Rosen, D. R., Martin-Morris, L., Luo, L. and White, K. A (1989). A *Drosophila* gene encoding a protein resembling the human b-amyloid precursor. PNAS 86, 2478-2482.

Ruthmann, A. *Methoden der Zellforschung,* Franckh'sche Verlagshandlung, Stuttgart, 1966.

Saunders, A M., Strittmatter, W. J, Schmechel, D., George-Hyslop, P. H., Pericak-Vance, M. A., Joo, S. H., Rosi, B. L., Gusella, J. F., Crapper-MacLachlan, D. R., Alberts, M. J., et al. (1993). Association of apolipoprotein E allele epsilon 4 with late-onset familial and sporadic Alzheimer's disease. Neurology 43, 1467-1472.

Simons, M., Keller, P., De Strooper, B., Beyreuther, K., Dotti, C. G. and Simons, K. (1998). Cholesterol depletion inhibits the generation of beta-amyloid in hippocampal neurons. Proc. Natl. Acad. Sci. 95, 6460-6464.

Stapleton, D., Mitchelhill, K. I., Gao, G., Widmer, J., Michell, B. J., Teh, T., House, C. M, Fernandez, C. S. Cox, T., Witters, L. A. et al. (1996). Mammalian AMP-activated protein kinase subfamily. J. Biol. Chem. 271, 611-614.

Thornton, C., Snowden, M. A. and Carling, D. (1998). Identification of a novel AMP-activated protein kinase beta subunit isoform that is highly expressed in skeletal muscle. J. Biol. Chem. 273, 12443-12450.

Torroja, L., Luo, L. and White, K. (1996). APPL, the *Drosophila* member of the APP family, exhibits differential trafficking and processing in CNS neurons. J. Neurosci. 16, 4638-4650.

Towbin, H, Staehelin, T and Gordon, J. (1979). Electrophoretic transfer of proteins from polyacrylamide gels to nitrocellulose sheets: procedure and some applications. Proc. Nat. Acad. Sci 76, 4350-4354.

Weisgraber, K. H. and Mahley, R. W. (1996). Human apolipoprotein E: the Alzheimer's disease connection. FASEB J. 10, 1485-1494.

Winder, W. W. and Hardie, D. G. (1999). AMP-activated protein kinase, a metabolic master switch: possible roles in type 2 diabetes. Am. J. Physiol. 277, E1-10.

Zheng, H., Jiang, M., Trumbauer, M. E., Sirinathsinghji, D. J., Hopkins, R., Smith, D. W., Heavens, R. P., Dawson, G. R., Boyce, S., Conner, M. W., et al. (1995). b-Amyloid precursor protein-deficient mice show reactive gliosis and decreased locomotor activity. Cell 81, 525-531

The invention claimed is:

1. A transgenic *Drosophila* whose genome is homozygous for the loechrig (loe) allele and homozygous for the *Drosophila* β-amyloid precursor-like deletion allele (Appl$^d$), wherein said transgenic *Drosophila* exhibits enhanced vacuolization, sterility in female *Drosophila*, neurodegeneration, accumulation of fatty acids in the brain and reduction of cholesterol ester.

* * * * *

UNITED STATES PATENT AND TRADEMARK OFFICE
CERTIFICATE OF CORRECTION

PATENT NO. : 7,554,003 B2
APPLICATION NO. : 11/544947
DATED : June 30, 2009
INVENTOR(S) : Doris Kretzschmar et al.

It is certified that error appears in the above-identified patent and that said Letters Patent is hereby corrected as shown below:

Please change the first inventor's name from "Kretschmar" to --Kretzschmar--.

Signed and Sealed this

Eighteenth Day of August, 2009

David J. Kappos
*Director of the United States Patent and Trademark Office*